United States Patent [19]
Bhitiyakul

[11] Patent Number: 5,941,854
[45] Date of Patent: Aug. 24, 1999

[54] INTRAVENOUS CATHETER

[76] Inventor: Somsak Bhitiyakul, 41 Tall Oaks Dr., Kingston, N.Y. 12401

[21] Appl. No.: 09/122,370

[22] Filed: Jul. 27, 1998

Related U.S. Application Data

[63] Continuation-in-part of application No. 08/359,567, Dec. 19, 1994.

[51] Int. Cl.⁶ ..................................................... A61M 5/00
[52] U.S. Cl. ........................... 604/168; 604/195; 604/900
[58] Field of Search ..................................... 604/168, 164, 604/165, 195, 192, 198, 263, 900

[56] References Cited

U.S. PATENT DOCUMENTS

| | | | |
|---|---|---|---|
| 5,000,740 | 3/1991 | Ducharme et al. | 604/168 X |
| 5,120,319 | 6/1992 | Van Heugten et al. | 604/168 |
| 5,496,281 | 3/1996 | Krebs | 604/900 X |
| 5,575,777 | 11/1996 | Cover et al. | 604/168 X |
| 5,685,855 | 11/1997 | Erskine | 604/168 |
| 5,704,914 | 1/1998 | Stocking et al. | 604/195 X |

*Primary Examiner*—John D. Yasko
*Attorney, Agent, or Firm*—Charles J. Brown

[57] ABSTRACT

In an intravenous catheter wherein a syringe needle and surrounding sheath are inserted into a vein so that blood flows through the needle into a transparent hollow push-pull element fixed on the needle remote from its point to indicate proper vein insertion, and the needle is then withdrawn from the sheath and from a vial on the end of the sheath so that blood back-flows into the vial before intravenous fluid is introduced through a side port in the vial into the vein, the vial opening being covered with an elastomeric diaphragm through which the needle is initially pierced and which self-seals when the needle is withdrawn therefrom, the improvement of a protective enclosure for the needle wherein a housing attachable to the vial surrounds the push-pull element so that the point of the needle is enclosed within that housing when the needle is withdrawn through the diaphragm.

7 Claims, 2 Drawing Sheets

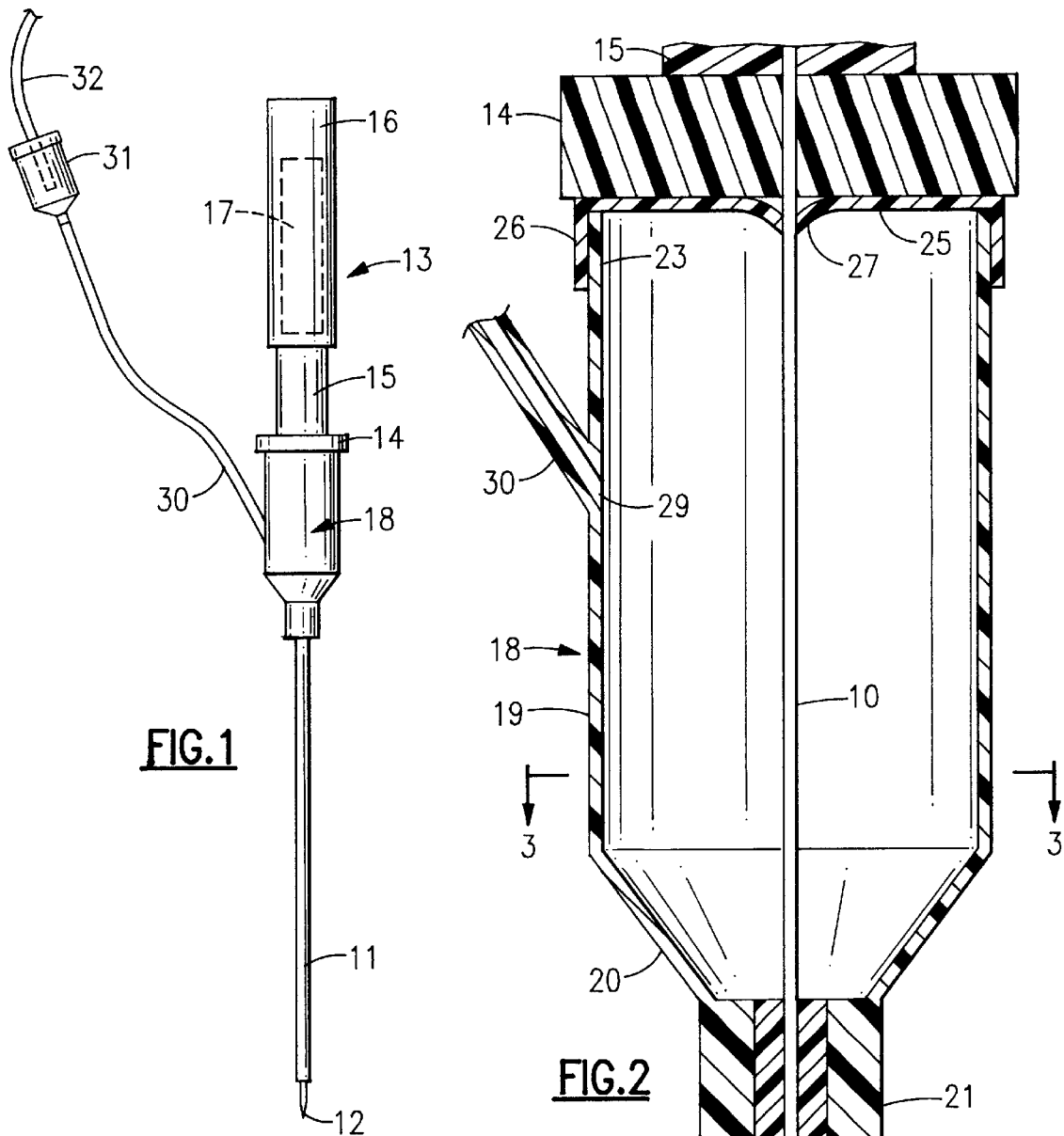
FIG.1
FIG.2
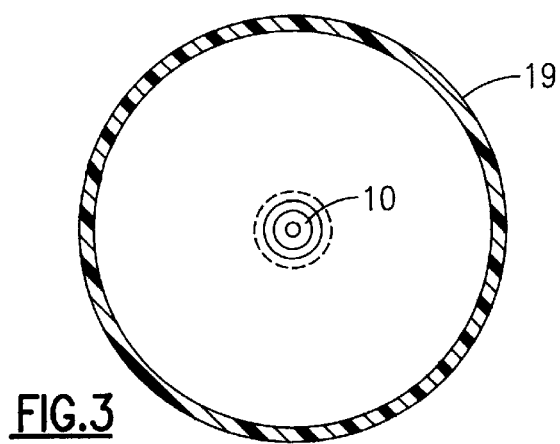
FIG.3

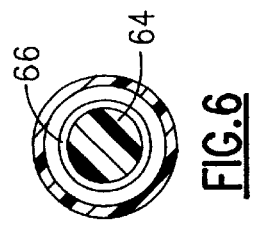
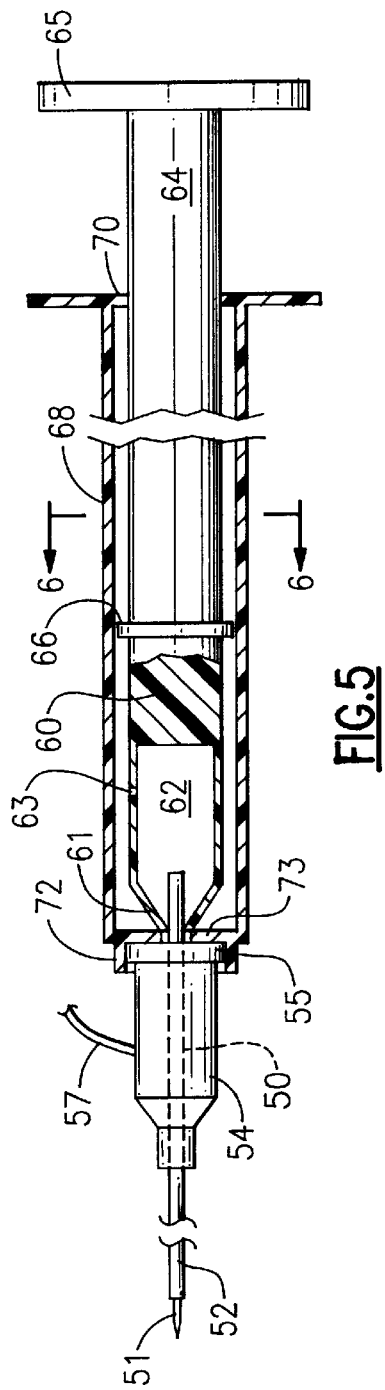
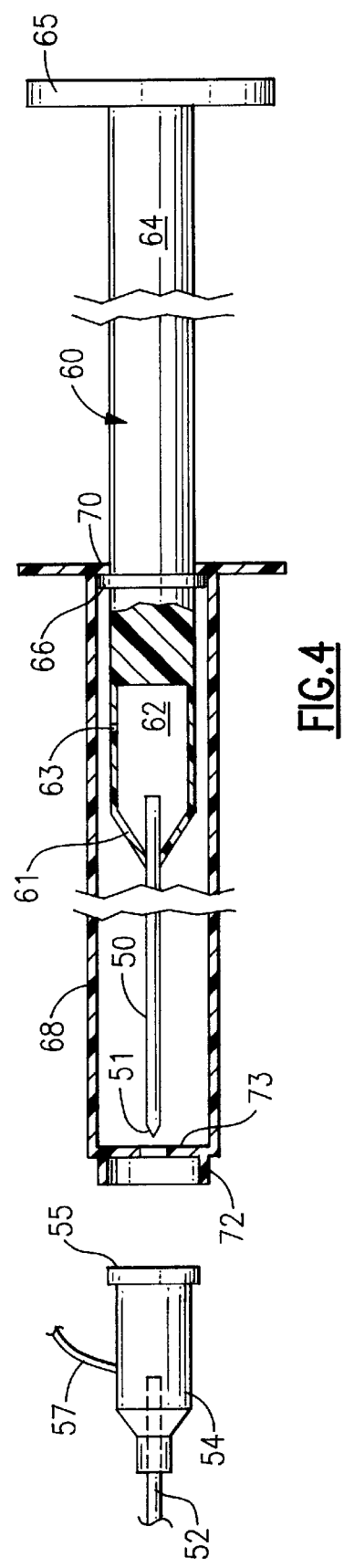

५,९४१,८५४

INTRAVENOUS CATHETER

CROSS REFERENCE TO RELATED APPLICATION

This application is a continuation-in-part of my co-pending application entitled METHOD OF INTRAVENOUS INJECTION AND METHOD THEREFOR, filed Dec. 19, 1994 and assigned Ser. No. 08/359,567.

BACKGROUND OF THE INVENTION

Conventional intravenous catheter apparatus includes a hollow syringe needle and a close-fitting surrounding sheath from which a point of the needle initially projects. The needle point and sheath are inserted into a vein so that blood back-flows through the needle into a transparent hollow push-pull element, usually cylindrical and somewhat elongated, fixed on the needle remote from its point. The appearance of blood within that transparent element indicates that the needle and sheath have been properly inserted in the vein. Typically there is a cylindrical elongated vial coaxially located on the end of the sheath and the needle initially extends coaxially through a circular end opening in the vial and through the sheath. After proper insertion in the vein the needle is then withdrawn from the sheath and from the vial through the opening in the vial and is discarded. The end of a flexible tube is then fitted into the vial opening to communicate with a source of intravenous fluid.

This conventional intravenous catheter design has been improved as described in my co-pending parent application by providing a diaphragm over the end of the vial through which the needle is initially inserted. Blood which back-flows into the vial after the needle is removed cannot advance farther beyond the diaphragm and leakage of blood from the vial prior to introduction of the intravenous fluid is thereby prevented.

However, a wholly separate problem remains. that is that the unprotected point of the removed needle withdrawn from the sheath and contaminated with blood can be a source of If accidental injury. The principal purpose of the present invention is to provide a protective enclosure for the needle to prevent accidental injury of that kind.

SUMMARY OF THE INVENTION

The invention constitutes an improvement in an intravenous catheter. In such a catheter a syringe needle is insertable within a sheath to an advanced position where a point on the needle projects from one end of the sheath. On that end of the needle remote from its point is a hollow push-pull element which is at least partly transparent and which receives blood through the needle to indicate proper vein insertion. An intravenous fluid receiving vial extends from an end of the sheath opposite the end from which the needle is projectable with a fluid receiving port in a wall of the vial. The needle is insertable through a diaphragm covering an end of the vial opposite the sheath which self seals when the needle is withdrawn therefrom. In accordance with the invention a protective enclosure for the needle is provided. The enclosure includes a housing around that part of the push-pull element which is hollow and within which the push-pull element is movable from a retracted position where the needle point is inside the housing to the above-mentioned advanced position where the needle projects from the sheath. The housing permits visibility therethrough into the transparent push-pull element. On one end of the housing is a collar releasably attachable to the vial end covered by the diaphragm. At the housing end opposite the collar is an annulus through which the push-pull element slidably projects. By this structure the needle can be withdrawn from the vial and the housing can be removed at its collar from the vial with the needle point protectively enclosed within the housing.

The protective enclosure for the needle may include a stop on the push-pull element inside the housing engagable with the annulus to prevent withdrawal of the push-pull element from the housing beyond the retracted position. On the inside of the housing a wall may be provided adjacent the collar which is engagable with the vial to prevent excessive projection of the needle point beyond the sheath in the advanced position. The housing may be at least partially transparent to permit visibility therethrough. The hollow push-pull element may include a vent opening through which air can escape as the hollow push-pull element receives blood. The vial may be cylindrical and elongated, the vial end covered by the diaphragm may be circular and located at an end of the cylindrical vial opposite the sheath, and the sheath and vial may be coaxial.

BRIEF DESCRIPTION OF THE DRAWINGS

FIG. 1 is an overall view of one form of the improved catheter;

FIG. 2 is an enlarged longitudinal fragmentary section principally of the vial of the catheter of FIG. 1;

FIG. 3 is an enlarged cross section taken along the line 3—3 of FIG. 2;

FIG. 4 is an enlarged longitudinal fragmentary section party broken away of the protective enclosure means of the present invention showing the push-pull element and needle in their retracted position where the needle point is inside the housing;

FIG. 5 is an enlarged longitudinal fragmentary section partly broken away showing the housing attached to the vial with the needle in the advanced position; and FIG. 6 is an enlarged lateral section taken along the line 6—6 of FIG. 5.

DESCRIPTION OF PREFERRED EMBODIMENTS

Referring to FIGS. 1 to 3 a hollow metal syringe needle 10 is closely surrounded by a plastic sheath 11 so that a pointed end 12 of the needle 10 initially projects slightly from the end of the sheath 11. Since the needle 10 and surrounding sheath 11 are to be inserted into a vein the end of the sheath 11 adjacent the projecting pointed end 12 of the needle 10 may be faired around the needle so as to minimize a sheath edge which might interfere with such insertion. An elongated transparent hollow push-pull element 13 is fixed on the needle end remote from its point 12. The push-pull element includes a circular flange 14 which appears in FIG. 2, a cylindrical central section 15 and a cylindrical transparent hollow end portion 16 adapted to be grasped by the fingers of the nurse or doctor. Within the transparent end portion 16 is a chamber 17 into which the interior of the needle 10 communicates. When the needle and surrounding sheath are inserted into a vein, blood flows through the needle 10 into the chamber 17 in the transparent end portion 16 to indicate proper vein insertion. The push-pull element 13 and its component parts comprising the flange 14, the central section 15 and the end portion 16 are of unitary molded plastic construction.

On the end of the sheath 11 remote from the point 12 of the needle 10 is a cylindrical vial 18 shown in detail in FIGS.

2 and 3. It includes a cylindrical body 19, a funnel portion 20 converging to a ferrule portion 21 surrounding the end of the sheath 11. There is a circular opening in the vial 19 at the end of the body portion remote from the funnel portion 20 defined by a circumferential body end portion 23. In prior art catheter designs the needle 10 is withdrawn from the sheath 11 and from the vial 18 through the opening defined by the vial body end portion 23 and is discarded. The nurse or doctor holds the push-pull element 13 with the fingers of one hand to pull the needle 11 out while grasping the vial 18 with the fingers of the other hand to keep the sheath 11 in place in the vein. The next step in this prior art practice is to insert the end of an intravenous fluid tube into the circular opening in the vial body 18 defined by the end portion 23. In the interim blood back-flows through the sheath 11 into the vial 18 and can leak outwardly through the opening defined by the vial body end portion 23 before the intravenous tube can be connected.

The apparatus for preventing such blood leakage from the vial opening comprises a cover on the vial opening with a circular elastomeric diaphragm 25 having a rim 26 which fits about the end portion 23 of the vial body 18 and may be glued in place. In the assembly of the apparatus the needle 10 is factory-fitted through the center of the diaphragm 25 by piercing the diaphragm to form a hole in the diaphragm which is defined by an encircling lip 27 resiliently gripping the needle 10. When the needle 10 is withdrawn from the diaphragm 25 the encircling lip 27 contracts resiliently to eliminate the hole in a self-sealing fashion. Any blood which flows into the vial 18 after the needle 10 is withdrawn is prevented from leaking out of the vial by the diaphragm 25.

Since the circular end opening in the vial body 19 defined by the end portion 23 is permanently closed by the diaphragm 25 it is not possible to insert the end of an intravenous tube into that opening to introduce intravenous fluid through the vial 18 and sheath 11 into the vein. Therefore a port 29 separate form the opening covered by the diaphragm 25 is provided in the vial 18 preferably in the cylindrical side of the vial body portion 19 as shown in FIG. 2. The end of a flexible tube 30 is permanently inserted in the port 29 and at its remote end a conventional intravenous connector 31 is provided for selective connection with a tube 32 leading to a source of intravenous fluid.

In the operation of the catheter, the parts are preassembled in the factory as shown in FIG. 1 with the pointed end 12 of the needle 10 projecting slightly from the end of the sheath 11. The flange portion 14 of the push-pull element 13 at this point is flush against the outside of the diaphragm 25 as shown in FIG. 2. The nurse or doctor grasps the vial 18 and push-pull element 13 with the fingers of one hand and inserts the end of the needle 10 and sheath 11 into the patient's vein. As a consequence blood back-flows out through the interior of the needle 10 and into the chamber 17 in the transparent end portion 16 of the push-pull element 13. The appearance of blood in the chamber 17 indicates that the needle and sheath are properly in place in the vein. The nurse or doctor then grasps the vial 18 with the fingers of one hand and the push-pull element 13 with the fingers of the other hand and pulls the push-pull element 13 out so that the needle 10 is withdrawn out of the sheath 11 and vial 18 and finally out of the central pierced hole in the diaphragm 25. That hole instantly closes as the lip 27 contracts resiliently.

The used push-pull element 13 and needle 10 are then discarded but while that is happening blood is entering the vial 18 through the sheath 11. However it is prevented from leaking out of the vial 18 by the diaphragm 25. The connector 31 may have been preconnected to the tube 32 leading to a source of intravenous fluid or the connector 31 may be so connected after the push-pull element 13 and needle 10 are discarded, but in any case the making of that connection prevents leakage of blood through the flexible tube 30. When the intravenous fluid source is opened the fluid flows through the flexible tube 30, into the vial 18 and then through the sheath 11 into the patient's vein.

Turning now to FIGS. 4 to 6, an embodiment of the invention as shown which provides protective enclosure means for the needle to prevent accidental injury particularly after the needle is withdrawn from the vial and is contaminated with blood from its prior use. As in the previous embodiment, a needle 50 has a pointed end 51 projecting from a sheath 52. A generally cylindrical vial 54 is attached to the end of the sheath 52. At one end of the vial 54 is a circular elastomeric diaphragm 55 through which the needle can be inserted. As described previously the hole then formed in the diaphragm 55 is self closing when the needle is withdrawn so as to prevent leakage of blood from the vial 54. A flexible tube provides a port 57 in the side of the vial 54 for connection to a source of intravenous fluid.

All of these elements so far described in relation to the embodiment of FIGS. 4 to 6 are identical to the corresponding elements in the embodiment of FIGS. 1 to 3 both in structure and in function. In the embodiment of FIGS. 4 to 6, protective enclosure means for the needle 50 are provided which prevent injury to personnel after the contaminated needle 50 is withdrawn and discarded.

Secured to the end of the needle 50 remote from its point 51 is a generally cylindrical hollow push-pull element 60. The push-pull element 60 has a conical end portion 61 where it is secured to the needle 50. Preferably the pushpull element 60 is completely transparent so that a user may see into a hollow chamber 62 formed therein and observe whether it contains blood from the patient. The chamber 62 is preferably confined to an end section of the push-pull element 60 adjacent the end portion 61 connected to the needle 50. Since blood is to enter the chamber 62 in the operation of the catheter, it is necessary to provide a small vent hole 63 allowing for escape of air as the chamber 62 fills with blood. The vent hole 63 is preferably of a location and small size sufficient to prevent any blood to pass therethrough. As shown in FIGS. 4 and 5 the push-pull element 60 includes a solid section 64 beyond the chamber 62 and at its outer extremity is a flange 65. Formed about the solid portion 64 of the push-pull element 60 is a circumferential stop 66. As shown in FIG. 6, the cross sections of the solid portion 64 of the push-pull element 60 and its stop 66 are circular.

A cylindrical housing 68 is formed about the greater part of the length of the push-pull element 60, both around the chamber 62 and its solid portion 64. The push-pull element 60 is movable from a retracted position shown in FIG. 4 where the point 51 on the needle 50 is within the housing 68. In that retracted position the stop 66 engages a circular annulus 70 at the end of the housing 68 which prevents withdrawal of the push-pull element 60 from the housing 68 beyond that position.

At the opposite end of the housing 68 is a cylindrical collar 72 which fits firmly over the end of the vial 54 about which the diaphragm 55 is fitted. Within the housing 68 is an annular wall 73 through which the needle 50 may loosely pass.

As shown in FIG. 4, the length of the cylindrical housing 68 is such that the needle 50 can be withdrawn from the vial 54 and the housing 68 can be removed at its collar 72 from the vial 54 with the needle point 51 protectively enclosed within the housing 68.

In the operation of the embodiment of the intravenous catheter shown in FIGS. 4 to 6, the clean needle 50 is initially within the housing 68 prior to use. The first step involves placing the collar 72 of the housing 68 over the end of the vial 54 and its diaphragm 55 in a snug fit which in effect leaves those parts physically attached. By applying a force to the left on the flange 65 of the push-pull element 60 as seen in FIG. 4, the needle 50 is advanced to the position shown in FIG. 5 where the needle point 51 has pierced the center of the diaphragm 55 and proceeded through the vial 54 and through the sheath 52. The end potion of the push-pull element 60 engages the annulus wall so that the push-pull element 60 cannot move farther into the cylindrical housing 68. This limit establishes the correct projection of the point 51 of the needle 50 beyond the end of the sheath 52 as shown in FIG. 5. The catheter of the invention is then ready for use.

Next the point 51 of the needle 50 and the adjacent end of the sheath 52 are inserted into a vein of the patient. Blood passes through the needle 50 into the chamber 62 and can be visually observed because the housing 68 and push-pull element 60 are both transparent. By pulling the flange 65 to the right from the position shown in FIG. 5 the push-pull element 60 is retracted until the point 51 of the needle 50 leaves the self-closing resilient hole in the diaphragm 55. The housing 68 is then withdrawn to the right so that the collar 72 is separated from the vial 54 and its diaphragm 55 as shown in FIG. 4. The housing 68 then encloses the entire needle 50 as shown in FIG. 4 so that no one can be injured by the needle point 51. The sliding fit between the solid portion 64 of the push-pull element 60 and the annulus 70 on the housing 68 is sufficiently tight so that the needle 50 is held in its full retracted position at all times after separation of the housing 68 from the vial 54.

The scope of the invention is to be determined from the following claims rather than the foregoing description of the preferred embodiments.

I claim:

1. In an intravenous catheter wherein a syringe needle is insertable within a sheath to an advanced position where a point on the needle projects from one end of the sheath, an at least partly transparent and hollow push-pull element is on one end of the needle remote from its point to receive blood through the needle to indicate proper vein insertion, and an intravenous fluid receiving vial extends from an end of the sheath opposite the end from which the needle is projectable with a fluid receiving port in a wall of the vial, the needle being insertable through a diaphragm covering an end of the vial opposite the sheath which self seals when the needle is withdrawn therefrom, protective enclosure means for the needle comprising a) a housing around that part of the push-pull element which is hollow and within which the push-pull element is movable from a retracted position where the needle point is inside the housing to said advanced position where the needle point projects from said sheath, b) the housing permitting visibility therethrough into the transparent push-pull element, c) a collar on one end of the housing releasably attachable to said vial end covered by said diaphragm, and d) an annulus on the housing end opposite the collar through which the push-pull element slidably projects, e) whereby the needle can be withdrawn from the vial and the housing can be removed at its collar from the vial with the needle point protectively enclosed within said housing.

2. An intravenous catheter according to claim 1 wherein a stop is on the push-pull element inside the housing engagable with the annulus to prevent withdrawal of the push-pull element from the housing beyond said retracted position.

3. An intravenous catheter according to claim 1 wherein a wall is on the inside of the housing adjacent the collar engagable with the vial to prevent excessive projection of the needle point beyond the sheath in the advanced position.

4. An intravenous catheter according to claim 1 wherein the housing is at least partly transparent to permit visibility therethrough.

5. An intravenous catheter according to claim 1 wherein the hollow push-pull element includes a vent opening through which air can escape as the hollow push-pull element receives blood.

6. An intravenous catheter according to claim 1 wherein the vial is cylindrical and elongated, the vial end covered by the diaphragm is circular and located at an end of the cylindrical vial opposite the sheath, and the sheath and vial end are coaxial.

7. In an intravenous catheter wherein a syringe needle is insertable within a sheath to an advanced position where a point on the needle projects from one end of the sheath, a transparent vented partly hollow push-pull element is attached to that end of the needle remote from its point to receive blood through the needle to indicate proper vein insertion, and an elongated cylindrical intravenous fluid receiving vial is on an end of the sheath opposite the end from which the needle is projectable with a fluid receiving port in a wall of the vial, the needle being insertable through a diaphragm covering a circular end of the vial opposite the sheath which self seals when the needle is withdrawn therefrom, the sheath and vial being coaxial, protective enclosure means for the needle comprising a) a cylindrical housing around that part of the push-pull element which is hollow and within which the push-pull element is movable from a retracted position where the needle point is inside the housing to said advanced position where the needle point projects from the sheath, b) the housing being at least partly transparent to permit visibility therethrough into the transparent push-pull element, c) a cylindrical collar on one end of the housing releasably attachable to said vial end covered by said diaphragm, d) a circular annulus on the housing end opposite the collar through which the push-pull element slidably projects, e) a circular stop on the push-pull element inside the housing engagable with the annulus to prevent withdrawal of the push-pull element from the housing beyond said retracted position, and f) a wall on the inside of the housing adjacent the collar engagable with the vial to prevent excessive projection of the needle point beyond the sheath in the advanced position, g) whereby the needle can be withdrawn from the vial and the housing can be removed at its collar from the vial with the needle point protectively enclosed within said housing.

* * * * *